United States Patent [19]

Kibblewhite

[11] Patent Number: 5,220,839

[45] Date of Patent: Jun. 22, 1993

[54] ULTRASONIC LOAD MEASURING DEVICE WITH CONTROL FEATURE

[75] Inventor: Ian E. Kibblewhite, Frazer, Pa.

[73] Assignee: Ultrafast, Inc., Malvern, Pa.

[21] Appl. No.: 797,535

[22] Filed: Nov. 25, 1991

Related U.S. Application Data

[62] Division of Ser. No. 572,415, Aug. 27, 1990, Pat. No. 5,131,276.

[51] Int. Cl.$^5$ ............................................. F16B 31/02
[52] U.S. Cl. ................................................... 73/761
[58] Field of Search ........................... 41/437; 73/761

[56] References Cited

U.S. PATENT DOCUMENTS

| | | |
|---|---|---|
| 3,306,100 | 2/1967 | Wilhelm et al. |
| 3,307,393 | 3/1967 | Kessler |
| 3,308,476 | 3/1967 | Klessattel |
| 3,759,090 | 9/1973 | McFaul et al. |
| 3,810,385 | 5/1974 | McFaul et al. |
| 3,812,709 | 5/1974 | Benson et al. |
| 3,822,587 | 7/1974 | Makino et al. |
| 3,918,294 | 11/1975 | Makino et al. |
| 3,969,810 | 7/1976 | Pagano |
| 3,969,960 | 7/1976 | Agano |
| 3,975,948 | 8/1976 | Makino et al. |
| 4,014,208 | 3/1977 | Moore et al. |
| 4,062,227 | 12/1977 | Heyman |
| 4,117,731 | 10/1978 | Heyman |
| 4,127,788 | 11/1978 | Daugherty |
| 4,294,122 | 10/1981 | Couchman |
| 4,344,216 | 8/1982 | Finkleston |
| 4,363,242 | 2/1982 | Heyman |
| 4,402,222 | 9/1983 | Olson et al. |
| 4,413,518 | 11/1983 | Jones |
| 4,471,657 | 9/1984 | Voris et al. |
| 4,569,229 | 2/1985 | de Halleux |
| 4,601,207 | 7/1986 | Steblay |
| 4,602,511 | 7/1986 | Holt |
| 4,760,740 | 8/1988 | Meisterling |
| 4,846,001 | 7/1989 | Kibblewhite |
| 4,899,591 | 2/1990 | Kibblewhite |

OTHER PUBLICATIONS

Final Report No. AFML-TR-78-137, "Acoustic-Elastic Fastener Preload Indicator", J. Couchman, Gen. Dynamics. Oct. 1978.

"Bulk Ultrasonic Transducer Employing Piezoelectric Film on Thin Metal Sheet", White, Chuang and Lee, IEEE Trans. on Sonics and Ultrasonics vol. SU-28 No. 1 pp. 8-13, Jan. 1981.

"Position and pressure effects in rf magnetron reactive sputter deposition of piezoelectric zinc oxide" Krupanidhi and Sayer, J. Applied Phys. 56(1), pp. 3308-3318, Jan. 1981.

"Sputtered C-Axis Inclined ZnO Films for Shear Wave Resonators" Wang and Lakin 1982 Ultrasonics Symposium, pp. 480-483.

"ZnO Transducers on InSB for low-temperature applications," Castonguay et al., J. Appled. Phys. 61(11), pp. 5199-5201, Jun. 1987.

"Cadmium Sulphide and Zinc Oxide Thin-Film Transducers", Foster et al., IEEE on Sonics and Ultrasonie, vol. Su-15, No. 1, pp. 28-41, Jan. 1968.

"Quantitative Effects of Substrate Tilt, Curvature, and Deposition Position on Orientation in ZnO Films", Howell et al., 1987 Ultrasonics Symposium, pp. 381-383.

"Toolbit Mounted Thin Film Zinc Oxide Sensors for Process Control in Lathe and Milling Machine Application" Bischoff, Ramalingam and Robbins, 1987 Ultrasonics Symposium, pp. 605-609.

"High Rate Deposition at Piezoelectric Zinc Oxide Films Using New Reactive Sputtering Technique", Tomonobu Hata et al, 1979 Ultrasonic Symposium, pp. 936-939.

"Preparation of Pb(Zr,Ti)O$_3$ thin films by sol gel processing: Elect., optical and electro-opt. prop.", Guanghua Yi et al, J. Appl. Phys. 64(5), Sep. 1, 1988, pp. 2717-2724.

F. Rollins, Jr., *Fastener Load Analysis Method, NASA Contractor Report (CR)-61354 (Apr. 2, 1971)*.

Primary Examiner—Hezron E. Williams
Assistant Examiner—Rose M. Finley
Attorney, Agent, or Firm—Ratner & Prestia

[57] ABSTRACT

A load indicating device and a method of using a load indicating device for monitoring the deformation in and imparting torque to a load bearing member are disclosed and claimed. An ultrasonic transducer, grown on one surface of a load bearing member, such as a fastener, is used to determine the length, stress or other tensile load dependent characteristic of the member using ultrasonic techniques.

42 Claims, 4 Drawing Sheets

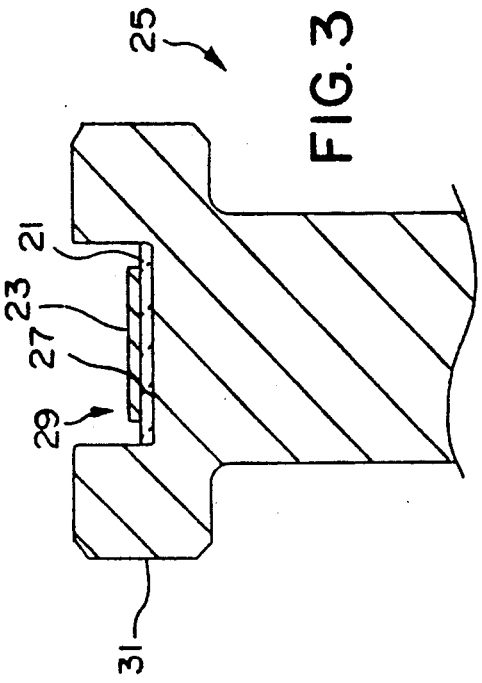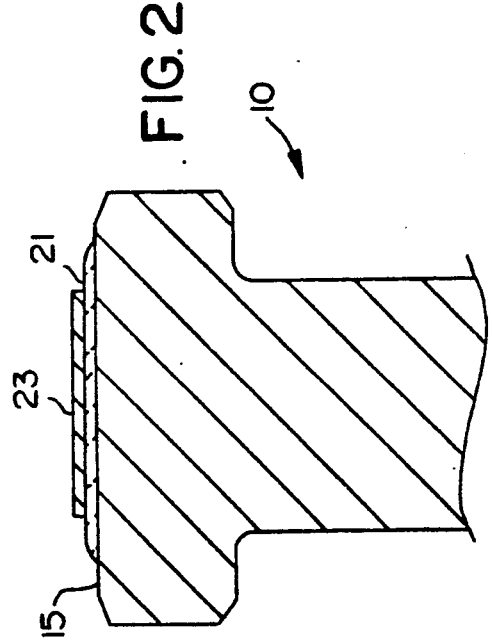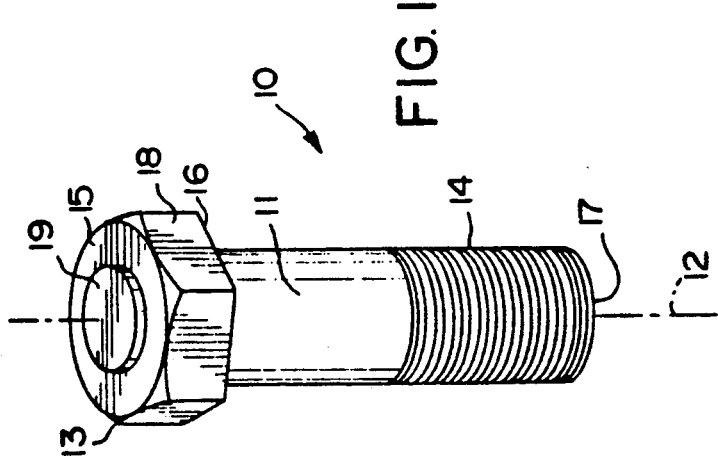

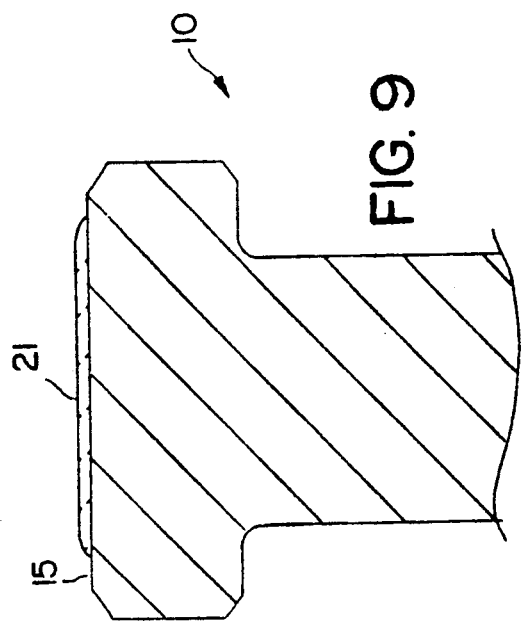
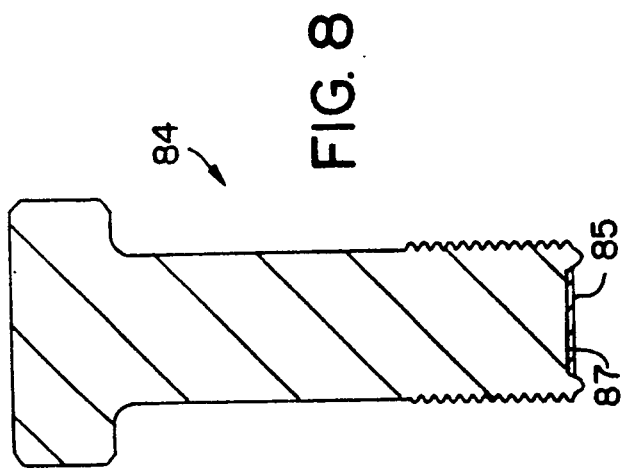
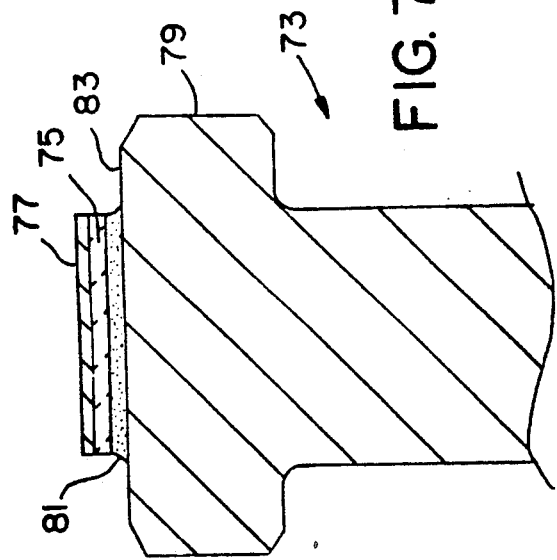

ULTRASONIC LOAD MEASURING DEVICE WITH CONTROL FEATURE

This application is a division of application Ser. No. 07/572,415, filed on Aug. 27, 1990, now U.S. Pat. No. 5,131,276.

BACKGROUND OF THE INVENTION

This invention relates to load indicating members and, more particularly, to load indicating members, such as fasteners, having ultrasonic transducers.

In many operations, it is desirable to determine the amount of longitudinal load experienced by a longitudinally stressed member. This information is particularly useful when the longitudinally stressed member is a fastener since the measurement of longitudinal stress provides a verification of the existence of a proper joint.

Many prior art techniques have been developed to indicate the amount of longitudinal stress experienced by a fastener by providing a load indicating feature to the fastener itself. This is usually done by interconnecting one end of an elongated member, such as a pin, to a portion of a fastener. While each of the various pin-type load indicating members and load measuring devices known in the art provides its own advantages in terms of accuracy, ease of manufacture, or ease of reading, they are still expensive to manufacture, since they each require extensive modifications and the addition of a centrally located pin-member. As a result, such load indicating members are only selectively used in practice, either where there is a specific immediate diagnostic need or where there is a serious recognized safety hazard involved. These members are simply too expensive for routine use in assemblies which may only occasionally benefit from such monitoring.

An alternative approach to measuring the elongation of a member or fastener is to use an ultrasonic measurement device. Typically, this is done by removably interconnecting an ultrasonic transducer to one end of the fastener being measured, usually the head of a bolt. In order to obtain a reliable indication., the head of the bolt must be ground extremely flat and a reliable ultrasonic transmission media must be applied to the head of the bolt. The transducer must be properly positioned on the bolt and held in position while the measurements are being taken. Various examples of techniques and apparatuses using this method are known in the art. Furthermore, the prior art teachings include the notion of combining the measuring device with a tightening tool so that the information gained from measuring the elongation of the bolt can be used for determining when to shut off the tool or, alternatively, for monitoring the tightening process to determine whether a proper joint has been formed.

While the above-mentioned products and apparatuses can provide reliable information about the fastener and joint, they are in very limited use. This is mainly because the bolt must be carefully manufactured and must be easily accessible to the instrumentation. Thus, ultrasonic tension measurement is recognized as a highly accurate laboratory tightening method for calibration, application testing and for tightening very critical joints. It is replacing strain gage bolts in several calibration and critical quality control applications. However, practical difficulties associated with taking ultrasonic tension measurements have prevented its application as a general assembly tightening strategy. These practical difficulties include: difficulty in maintaining reliable acoustic coupling during tightening; difficulties presented by equipment expense and complexity; and difficulties presented by experimental determination of parameters for each joint.

Some attempts have been made to overcome the above-mentioned difficulties by incorporating a piezoelectric or other ultrasonic transducer into the member itself. Examples of such members are disclosed, for example in U.S. Pat. No. 4,127,788 issued Nov. 28, 1978 to Daugherty and U.S. Pat. No. 4,294,122 issued Oct. 13, 1981 to Couchman. Each of these disclosures provides an instrumented load bearing fastener which has been modified to incorporate a stress indicating feature. However, like the pin-type fasteners described previously, these instrumented fasteners are greatly modified in order to accept large and complicated ultrasonic sensing devices. They are therefore prohibitively expensive for wide spread use.

U.S. Pat. No. 4,846,001, Kibblewhite, teaches the use of a thin piezoelectric polymer film sandwiched between two thin electrodes, which is permanently, mechanically and acoustically coupled to the upper surface of a member and is used to determine the length, tensile load, stress, or other tensile load dependent characteristic of the member by ultrasonic techniques. While the invention represents a significant advance over the prior state of the art in terms of performance, ease of manufacture and manufacturing cost, there are disadvantages with a transducer of this construction. These disadvantages relate to environmental performance, in particular the maximum temperature limitations of the polymer material which restricts its application, and the possibility of the transducer, fixed to the fastener with adhesive, coming loose and causing an obstruction in or damage to a critical assembly.

Most stressed members, such as fasteners, for example, are subject to varying stresses along the length of the member. It is therefore often desirable to determine the stress in a specific part of the member. The use of load indicating members incorporating artificial reflectors provides a means of measuring a load dependent characteristic over a specific part of the member. U.S. Pat. No. 4,569,229, de Halleux, teaches of a method of manufacturing and measuring stress in a member incorporating artificial ultrasonic reflectors. Steblay, U.S. Pat. No. 4,601,207 discloses a mine roof bolt and a means of measuring the strain in a mine roof bolt incorporating an artificial reflector, wherein the artificial reflector is a hole drilled radially through the bolt at a predetermined distance from the head of the bolt.

All the above-mentioned ultrasonic methods of determining stress in a load indicating member require a zero load measurement in addition to the measurement taken under the desired loaded condition in order to determine the absolute load in the member. Furthermore, all use a direct or indirect measurement of the out and return time of flight of a longitudinal ultrasonic wave. Holt, U.S. Pat. No. 4,602,511, teaches of a method which uses the times of flight of both longitudinal and transverse waves to determine the stress in a member without taking a zero load measurement. This is desirable in the measurement of tensile load in previously installed fasteners, for example.

The use of transverse ultrasonic waves, however, requires both a transducer capable of generating transverse waves and an acoustic coupling media capable of transmitting transverse waves into the member. Special acoustic couplants are required with temporarily attached transducers, since transverse waves cannot generally be transmitted through liquids. Although adhesives can transmit transverse ultrasonic waves, generation of transverse waves using the polymer film transducers, disclosed by Kibblewhite in U.S. Pat. No. 4,846,001, has not been demonstrated.

What is desired, therefore, is an ultrasonic transducer permanently attached to a fastener, to provide accurate tightening information during assembly, which can not come loose and cause an obstruction in or damage to a critical assembly.

What is secondly desired is such ultrasonic transducer permanently attached to a fastener which can withstand the operating environment and, in particular, the operating temperature of the fastener, so that the fastener can be reused or, so that the load in the fastener can be measured periodically during the operation of the assembly in which the load indicating fastener is installed.

What is further desired is such ultrasonic transducer permanently attached to a fastener which is capable of transmitting both longitudinal and transverse waves for the measurement of stress in already installed fasteners.

What is also desired is such ultrasonic transducer permanently attached to a fastener which can be manufactured to direct ultrasonic waves toward artificial reflectors within the fastener.

What is further desired is such ultrasonic transducer permanently attached to a fastener which can be manufactured to generate high frequency ultrasonic waves, 10–500 MHz, for example, to provide improved accuracy in the measurement of ultrasonic out and return times of flight.

What is additionally desired is such ultrasonic transducer permanently attached to a fastener which can be manufactured to generate high frequency ultrasonic waves, 10–500 MHz, for example, to provide improved resolution for the detection of small ultrasonic artificial reflectors or small manufacturing defects.

What is even further desired is such ultrasonic transducer permanently attached to a fastener which does not require a separate high voltage polarization operation as part of its manufacturing process.

What is further additionally desired is such ultrasonic transducer permanently attached to a fastener which can be manufactured at low cost using high volume manufacturing methods.

SUMMARY OF THE PRESENT INVENTION

The present invention relates to load indicating members and, more particularly, to load indicating members such as fasteners, having ultrasonic transducers.

The present invention eliminates many of the disadvantages of the load indicating members of the prior art and provides additional features and advantages not previously available in load indicating members, load indicating fasteners and load indicating devices.

The load indicating member of the present invention includes a shank subject to elastic deformation when stressed longitudinally, and a first and second surface, each formed adjacent to one longitudinal end of the shank. A piezoelectric element permanently, mechanically and electrically interconnected with a first and second electrode means is disposed on the first surface of the shank, wherein the piezoelectric element is a thin oriented piezoelectric film grown on the first or second electrode means using a vapor deposition technique.

In the preferred embodiment, the piezoelectric element is a thin oriented film of zinc oxide (ZnO) and the first electrode means is the first surface of the member. Furthermore, in this preferred embodiment, the second electrode means is an electrically conductive metallic film. Additionally, in this preferred embodiment the load indicating member is a load indicating fastener having an enlarged head and the first surface is formed on the head of the fastener.

The method of making a load indicating member according to the present invention includes the steps of providing a smooth surface on one longitudinal end of the fastener; growing the piezoelectric oriented film element using a vapor deposition technique on the first electrode means; and permanently, mechanically and electrically interconnecting the second electrode means to the piezoelectric element so as to electrically isolate the second electrode means from the first electrode means.

An alternative method of making a load indicating member according to the present invention includes the steps of providing a surface on one longitudinal end of the fastener; growing the piezoelectric oriented film element using a vapor deposition technique on the second electrode means; and permanently, mechanically, electrically and acoustically interconnecting the piezoelectric element to the first electrode means so as to electrically isolate the first electrode means from the second electrode means.

The load measuring device according to the present invention provides a first contact means electrically engageable with the first electrode means, second contact means electrically engageable with the second electrode means, and an electronic measurement device responsive to electronic differential signals between the first and second electrode means such as to provide a measurement of the tensile load in the load indicating member when stressed longitudinally.

In the preferred embodiment the piezoelectric element may also provide a driving means for producing an ultrasonic signal such as to generate the electronic differential signals. Furthermore, in the preferred embodiment, the load indicating member is electrically conductive and the first contact means is electrically engaged with the first electrode means indirectly by engagement of the first contact means with the load indicating member.

The tightening tool according to the present invention includes first and second contact means electrically engageable respectively with the first and second electrode means, a load imparting means for inducing tensile load in the load bearing member, and a load measuring device responsive to the electrical differential signal such as to provide an accurate measurement of tensile load.

The tightening tool according to the present invention includes an electrically conductive fastener engagement means engageable with a load indicating fastener, a contact member engageable with a second electrode means of the load indicating fastener, a drive means imparting a torque on the fastener engageable means so as to rotatably drive the load indicating fastener, and a load measuring device responsive to the electrical differential signal received from the fastener engagement means and the contact member such as to provide an accurate measurement of the tensile load in the shank of the fastener when stressed longitudinally as a result of the tightening process.

The output of the load measuring device may be used to provide a continuous reading of the instantaneous tensile load of the fastener or, alternatively, may be used to determine when the fastening operation is complete or to provide an indication of the load in a previously tightened fastener. When the load indicating member is a fastener, the load measuring device may be used simultaneously with a fastener tightening tool or, alternatively, may be incorporated directly into the tightening tool. When the fastener tightening tool incorporating the load measuring device is of an automatic tightening type, the tensile load indication in the load measuring device may be combined with other parameters monitored by the fastener tightening tool, such as angle and torque, to determine when the tightening cycle is complete and to detect irregularities in the joint.

A primary object of the present invention is to provide an inexpensive load indicating member with an ultrasonic transducer which will remain attached during the operating life of the member. Another object of the present invention is to provide a load indicating member with an ultrasonic transducer which will withstand the operating temperature of the fastener without degradation of performance. Still another object of the present invention is to provide a load indicating member with an ultrasonic transducer which is capable of transmitting both transverse and longitudinal ultrasonic waves. Yet another object of the present invention is to provide a load indicating member with an ultrasonic transducer which can be manufactured to direct ultrasonic waves toward artificial reflectors within the load indicating member. Still another object of the present invention is to provide a load indicating member with an ultrasonic transducer which can be manufactured to generate high frequency ultrasonic waves to improve the measurement accuracy and resolution of the load measuring device.

These and other objects, features and advantages of the present invention will become apparent to those skilled in the art when the following exemplary detailed description of the present invention is read in conjunction with the drawings appended hereto.

BRIEF DESCRIPTION OF THE DRAWINGS

In the drawings, wherein like reference numerals refer to the like elements throughout:

FIG. 1 is a perspective view depicting an example of a load indicating member according to the present invention;

FIG. 2 in an enlarged sectional view illustrating the load indicating member of FIG. 1;

FIGS. 3 through 9 are views similar to FIG. 2 but illustrating alternative examples of load indicating members according to the present invention;

DETAILED DESCRIPTION OF THE PREFERRED EMBODIMENTS

Figure 6:
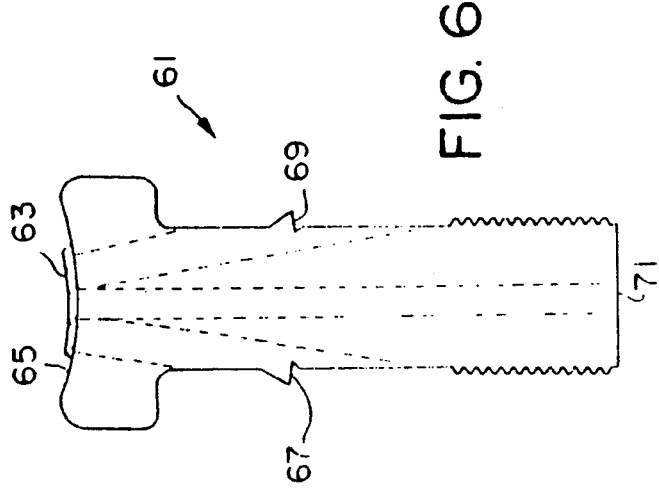

The present invention provides for a load indicating member comprising a shank and an ultrasonic transducer means coupled to the load indicating member. The ultrasonic transducer means can be coupled to the load indicating member at any appropriate location on the member. More than one ultrasonic transducer may be utilized in accordance with the present invention. For example, a first ultrasonic transducer for generating an ultrasonic drive pulse wave can be coupled to a first surface of the load indicating member so that the drive pulse is directed toward an acoustically reflective surface or a second ultrasonic transducer, and the second ultrasonic transducer, suitable for receiving echo waves from an acoustically reflective surface or the first ultrasonic transducer, can be coupled to the member at a different location on the member. However, the use of a single ultrasonic transducer for both generating the drive pulse wave and receiving the echo waves is preferred. Moreover, it is preferred that the ultrasonic transducer be grown directly on the first surface of the load indicating member using a vapor deposition technique such as to provide permanent, mechanical, electrical and acoustical interconnection to the first surface of the member to eliminate the need for an interconnection means, such as an adhesive, for example. The ultrasonic transducer means may also be located in a recess to protect the transducer means from environmental hazards.

The load indicating member can be formed from a bolt, rod, rivet, stud or other suitable structural element which has been modified to provide an indication of the tensile load, stress, elongation or other characteristic of the element during the tightening operation, as well as at various times during the life of the joint in which the element is installed. Moreover, the load indicating member can be made of metal, plastic or other appropriate material suitable for transmitting ultrasonic waves.

The load indicating member of the present invention may be used with a tightening tool, including a conventional power tool, which engages the load indicating member both electrically and mechanically, as can be appreciated by those skilled in the art. Furthermore, an electronic control device may be electrically interconnected with the ultrasonic transducer by techniques well known in the art. The electronic control device supplies and measures electronic signals of the ultrasonic transducer such as to provide an ultrasonic measurement of tensile load, stress or elongation of the shank of the load indicating member.

It will be appreciated by those skilled in the art that the tightening tool may be provided with a display device for displaying ultrasonic measurement of the tensile load, stress, elongation or member identification obtained during operation. Alternatively, the tightening tool may be adapted to use the information continuously supplied by the electronic control device to determine when a predetermined amount of tensile load or elongation has occurred and, therefore, when a tightening operation should be stopped. It will further be appreciated by those skilled in the art that the power tool chosen may, in a manner well-known in the art, monitor other characteristics of the joint being formed, such as the torque and the instantaneous angle of the load indicating member. An example of such a power tool may be found in U.S. Pat, No. 4,344,216, Finkelston, issued Aug. 17, 1982. This other information available from the power tool may be combined with the tensile load, stress, elongation or member identification information supplied by the electronic control device to provide a precisely controlled tightening operation wherein the various measured parameters are used directly to control the tightening sequence or to monitor the results of a tightening operation.

An example of an apparatus that may be used with the present invention for measurement of the time of flight of ultrasonic waves along the member is described in U.S. Pat. No. 4,846,001, Kibblewhite, issued Jul. 11, 1989, the entire disclosure of which is accordingly incorporated by reference herein. Many different techniques for the measurement of time of flight are well-known in the art as a result of ultrasonic developments in the field of non-destructive testing. Most of the techniques are capable of providing the required resolution and accuracy. However, some of the techniques offer particular advantages in terms of the number of pulses for accurate measurement, circuit complexity and power consumption. The load indicating member of the present invention is preferably utilized with pulse-echo techniques, but other techniques known in the art, such as resonant techniques or acoustic emission stress measurement techniques, can also be utilized.

A clear understanding of the present invention can be had by reference to the accompanying drawings. Although specific forms of the invention have been selected for illustration in the drawings themselves, the descriptions thereof are not intended to limit the scope of the present invention.

FIGS. 1 and 2 illustrate one preferred embodiment of a load indicating member and, more particularly, a fastener 10 adapted for measuring strain in fastener 10. The fastener 10 in this preferred embodiment is a bolt comprising a shank 11 having a longitudinal axis 12 and a predetermined longitudinal length. The shank 11 is adapted to be subjected to longitudinal strain along the longitudinal axis 12. A head 13 is formed on one longitudinal end of the shank 11 and threads 14 are formed at the other longitudinal end. The head 13 has an end surface 15 formed on the end portion of the head 13, and a shoulder 16 is formed between the head 13 and the shank 11. A lower surface 17 is formed at the opposite end of the shank 11. The head 13 is also provided with a wrenching or tool engagement surface 18, such as a hexagonal wrenching surface disposed about the periphery thereof.

It will be appreciated by those skilled in the art, that a piezoelectric element must be sandwiched between two electrically conductive electrodes, wherein the electrodes distribute and collect electrical charge, in order to function as an ultrasonic transducer 19. In the preferred embodiment, fastener 10 is metallic and, therefore, a surface of fastener 10 can function as a first electrode.

Preferably, as illustrated in FIG. 2's enlarged and sectional view, end surface 15 is manufactured to be a smooth surface, with a surface finish typically better than 2 micron, and piezoelectric element 21 is formed directly on end surface 15 by growing, using a vapor deposition technique, an oriented film of a material known to exhibit piezoelectric properties when grown in this manner.

Zinc oxide (ZnO), aluminum nitride (AlN), and cadmium sulfide (CdS) are among materials documented in the references cited which exhibit the required piezoelectric properties. These materials are used in the manufacture of electronic components such as surface acoustic wave, bulk acoustic wave and resonating devices. Experimental application of these materials in acoustic emission and non-destructive testing applications, discussed by White, Chuang and Lee, "Bulk Ultrasonic Transducer Employing Piezoelectric Film on Thin Metal Sheet", IEEE Trans. on Sonics and Ultrasonics, Vol. SU-28, No. 1, pp. 8-13 (January 1981), has also been reported. While piezoelectric element 21 is zinc oxide in the preferred embodiment, it will be appreciated by those skilled in the art that alternative materials may be substituted, particularly if they possess desirable properties such as improved piezoelectric properties, improved environmental resistance or lower manufacturing cost, for example.

Deposition techniques, suitable for growing piezoelectric oriented films, are known to those skilled in the art and are extensively documented in the references cited. In a reference by Krupanidhi and Sayer, "Position & Pressure Effects in RF Magnetron Reactive Sputter Deposition of Piezoelectric Zinc Oxide", J. Applied Phys. 56(11), pp. 3308-3318 (December 1984), growth techniques such as spray pyrolysis, chemical vapor deposition, dc diode, dc and rf magnetron sputtering are documented as producing oriented piezoelectric films of zinc oxide exhibiting suitable properties. Deposition by sputtering has proved advantageous because highly oriented films can be obtained.

It will be appreciated by those skilled in the art, that preparation of the fastener or fastener surface may be desirable prior to forming the piezoelectric element on end surface 15 in FIG. 2 using a vapor deposition technique. Such preparation may include, for example, the application of coatings to improve electrical conduction or adhesion, chemical etching or cleaning.

Second electrode 23 of FIG. 2 is permanently, mechanically and electrically connected to the piezoelectric element 21. As interconnected, piezoelectric element 21 and second electrode 23 form transducer element 19 illustrated in FIG. 1. The second electrode 23 may be formed of a metallic layer deposited using a vapor deposition technique, a conductive ink or paint or, alternatively, a conductive foil may be bonded to piezoelectric element 21 with, for example, an adhesive. The second electrode 23 is interconnected to the piezoelectric element 21 such as to be electrically isolated from the first electrode, fastener end surface 15.

Since piezoelectric element materials are essentially electrical insulators, it will be appreciated by those skilled in the art that, in the preferred embodiment shown in FIG. 2, the effective transducer area of the piezoelectric element 21, manufactured in accordance with the present invention, is defined by the area of second electrode 23, since second electrode 23 functions such as to distribute and collect electrical charge over the surface of piezoelectric element 21. Consequently, accurate positioning or the use of masking techniques is not required during the manufacture of the piezoelectric element 21 in the above-described preferred embodiment of the present invention.

It will also be appreciated by those skilled in the art that the frequency characteristics of piezoelectric element 21 are dependent on the thickness of the element. It will be further appreciated by those skilled in the art that the film thickness can be controlled precisely using the above-described manufacturing process by controlling the growth rate and the growth time. Consequently, therefore, the frequency characteristics of piezoelectric element 21 can be controlled precisely over a wide range of frequencies. It will additionally be appreciated by those skilled in the art, that the use of higher frequency ultrasonic transducers can improve time of flight measurement accuracy by providing echo waveforms with faster rise and fall times and can improve resolution in the detection of small reflective surfaces or small fastener manufacturing defects through the reduced dispersion of ultrasonic waves of a shorter wavelength. In the preferred embodiment of the present invention, both the piezoelectric element thickness and the second electrode thickness in the range 1 to 50 micron are used and transducer frequencies in the range 1 to 500 MHz are used.

It is further documented in the references cited that the crystal inclination angle of piezoelectric oriented films can be controlled in the above mentioned manufacturing processes. In Wang and Lakin, "Sputtered C-axis inclined ZnO Films for Shear Wave Resonators", IEEE Ultrasonics Symposium, pp. 480–483 (1982), experimental results are documented demonstrating the feasibility of controlling the inclination angle and, through the control of inclination angle, the control of the fractional components of longitudinal and transverse ultrasonic waves generated by zinc oxide piezoelectric elements manufactured by vapor deposition techniques. The use of both longitudinal and transverse waves in the measurement of tensile load in a load indicating member, as disclosed by Holt in U.S. Pat. No. 4,602,511, permits the measurement of stress in a member without taking a zero load measurement. This is desirable in the measurement of tensile load in previously installed fasteners, for example.

Inventions of the prior art, Kibblewhite, U.S. Pat. No. 4,846,001 issued Jul. 11, 1989, and Couchman, U.S. Pat. No. 4,294,122 issued Oct. 13, 1981, require a mechanical, electrical and acoustical interconnection means to connect the piezoelectric element to the load indicating member, since the piezoelectric element is manufactured prior to interconnection to the load indicating member. This interconnection means is, for example, an adhesive. Difficulties in providing satisfactory interconnection means relate to the mechanical, electrical and acoustical requirements of the interconnection. Firstly, suitable interconnection materials which meet the adhesion requirements of many fastener applications, such as aircraft engines, for example, are not available. Secondly, since the interconnection material must electrically interconnect the piezoelectric element to the load indicating member, the interconnection material must either be electrically conductive or, alternatively, be sufficiently thin such as to capacitively couple the electrical signal from the piezoelectric element to the load indicating member. Thirdly, the interconnection means must be a suitable acoustic coupling media such as to provide a means of transmitting the ultrasonic wave from the piezoelectric element into the load indicating member. Inclusion of air bubbles, for example, greatly reduces the amplitude of the received echo signals. Hence, it will be appreciated by those skilled in the art, that the direct deposition of the oriented piezoelectric element of the present invention eliminates the above-described difficulties of the inventions of the prior art.

Piezoelectric film material of the prior art disclosed by Kibblewhite, U.S. Pat. No. 4,846,001 issued Jul. 11, 1989, are polymer materials, such as polyvinylidene fluoride or copolymer VF2/VF3. The piezoelectric properties of these materials are destroyed if they are exposed to temperatures in excess of 125 degrees C. There are many applications for load indicating fasteners in assemblies such as, for example, automobile and aircraft engines where critical fasteners experience much higher temperatures. Hence, load indicating members of the above-referenced invention or, the transducers on the load indicating members of the above-referenced invention, must be replaced during the servicing operation of the assembly in order to reassemble the assembly using the same ultrasonic tightening method. Additionally, at temperatures in the range 150 to 200 degrees C., the above-mentioned polymer materials melt allowing the electrode to come loose with a risk of obstruction in or damage to critical components in the assembly. Consequently, there is a reluctance by potential users to install load indicating members of the above-referenced invention in many assemblies. Piezoelectric materials of the present invention can withstand much higher temperatures than can piezoelectric polymer materials. The melting point of zinc oxide, for example, is 1975 degrees C.

A further disadvantage of the use of piezoelectric polymer materials, disclosed in the above-referenced invention, is the requirement for a separate high voltage polarization operation during manufacture. This high voltage polarization operation increases significantly the cost of the piezoelectric element. In the present invention, the piezoelectric elements are formed oriented and, therefore, high voltage polarization is not an operation in their manufacture.

The piezoelectric polymer materials of the above-referenced invention are, in theory, slightly more efficient than the materials of the present invention when used in ultrasonic pulse-echo applications. However, the transducers of the present invention are more effective at transmitting ultrasonic waves to and from the load indicating fastener as a result of the improved interconnection between the piezoelectric element and the fastener surface and the closer match in acoustic impedances of the piezoelectric element and the load indicating fastener. This improvement in transmission effectiveness more than compensates for the difference in material piezoelectric efficiencies. Moreover, large variations in overall transducer efficiencies are experienced with load indicating members of the above-referenced invention as a result of manufacturing variations in providing the interconnection means between the transducer means and the load indicating member. This interconnection means, and hence the resulting performance variations, are eliminated in the preferred embodiment of the present invention.

It should be noted, therefore, that manufacturing the piezoelectric element directly on the load indicating member using a vapor deposition technique of the present invention and the use of materials which can be used to form piezoelectric transducer elements in accordance with the present invention result in a load indicating member with a significant performance improvement over load indicating members of the prior art.

FIGS. 3 through 9 show alternative embodiments of the present invention. In the alternative embodiment illustrated in FIG. 3, end surface 27 is formed on load indicating member 25 in recess 29 in head 31. The recess 29 may be a tool engagement socket, a lightening hole or a shallow recess created for the purpose of protecting the piezoelectric transducer from environmental hazards.

Figure 4:
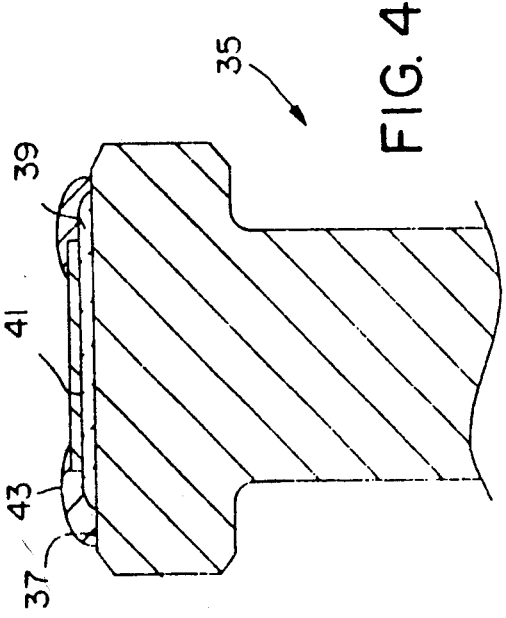

In yet another embodiment of the present invention, shown in FIG. 4, an additional layer 43 is formed to extend over the outer parts of second electrode 41, piezoelectric element 39 and end surface 37 of load indicating member 35 such as to exclude particles or contaminants which could cause electrical shorting between the second electrode 41 and the first electrode, which is end surface 37 in the embodiment shown in FIG. 4, and to protect piezoelectric element 39 from environmental hazards, such as solvents, which could degrade the performance of piezoelectric element 39.

Figure 5:
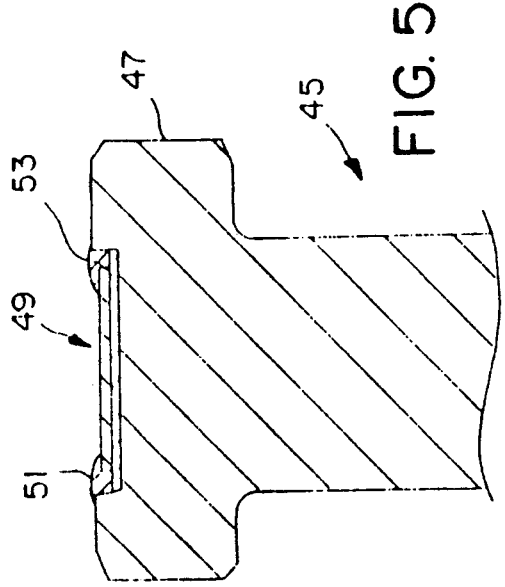

The embodiment shown in FIG. 5 is a fastener 45 with a shallow recess 49 in head 47. In this embodiment, additional layer 51 is used to protect the piezoelectric element 53 from environmental hazards.

In all the above-described embodiments of the present invention, the part of the piezoelectric element functioning as an ultrasonic transducer is essentially flat, being formed by vapor deposition on an essentially flat surface of the load indicating member. FIG. 6 shows an example of an embodiment of the present invention, wherein piezoelectric element 63 is formed on a surface 65 of load indicating member 61 such as to provide an ultrasonic transducer to direct longitudinal, transverse or longitudinal and transverse ultrasonic waves toward alternative reflective surfaces 67 and 69 as well as toward surface 71 of load indicating member 61. It will be appreciated by those skilled in the art that there are numerous alternative end surface configurations on which piezoelectric elements of the present invention can be formed such as to allow ultrasonic waves to be directed toward or focused at specific reflective surfaces.

An alternative embodiment of the present invention, wherein the piezoelectric element is formed on the second electrode is illustrated in FIG. 7. In this embodiment, piezoelectric element 75 is first formed on second electrode 77, wherein second electrode 77 is a thin electrically conductive material such as, for example, metal foil. Piezoelectric element 75 is then permanently, mechanically, electrically and acoustically interconnected to surface 83 on head 74 of load indicating member 73 with interconnecting means 81 which may be, for example, an adhesive. An advantage of the embodiment of the present invention shown in FIG. 7 may be ease of manufacture of the piezoelectric element 75. This embodiment does not, however, have the previously-described advantages which result from forming the piezoelectric element directly on the surface of the load indicating member.

In the above-described embodiments of the present invention, the ultrasonic transducer means is interconnected to a surface at the longitudinal end of the load indicating fastener on which the head is formed. It will be appreciated by those skilled in the art, that the transducer means could, alternatively, be interconnected to the other longitudinal end of the load indicating fastener, as illustrated in the embodiment of the present invention illustrated in FIG. 8. This embodiment may be preferable if, for example, during fastener installation a nut, used in conjunction with the load indicating member, is rotated by the tightening tool in order to induce tensile load. In this embodiment of the invention, transducer 85 is formed on end surface 87 of fastener 84.

All the above-described embodiments have a second electrode mechanically and electrically interconnected with the oriented piezoelectric film. FIG. 9 shows an embodiment of the present invention similar to the embodiment shown in FIG. 2 but without a permanently interconnected second electrode. With this embodiment, the second electrode is provided by an electrically conductive plate, electrically connected to the load measuring device, brought in contact with or in close proximity to the oriented piezoelectric film during ultrasonic measurement of tensile load, elongation or stress.

Figure 10:
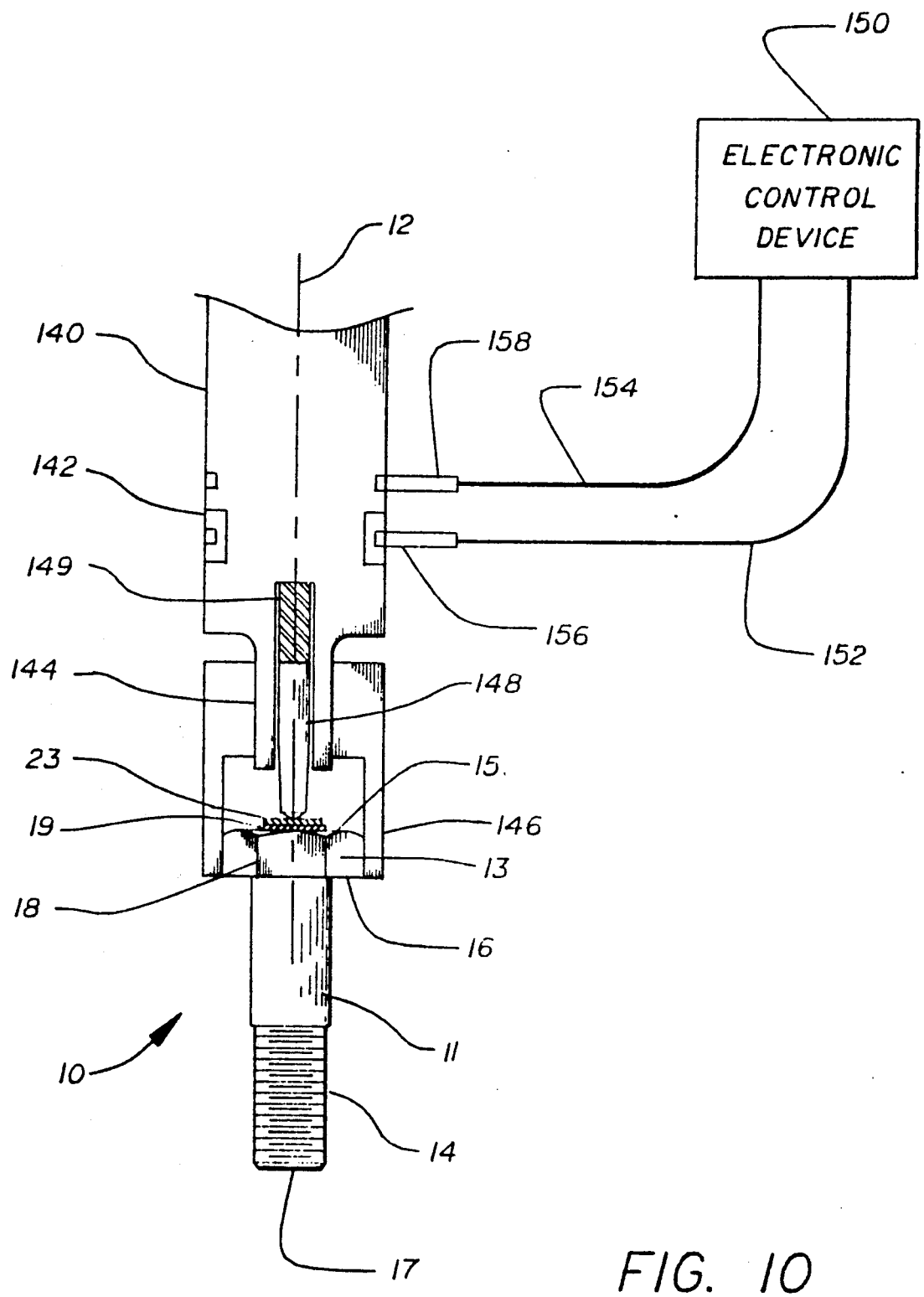
FIG. 10 is a partially schematic and partially cutaway side view depicting a load indicating member according to the present invention engaged with a fastener tightening tool.

Referring to FIG. 10, an example of a load indicating fastener 10 according to the present invention and described above is shown with a fastener tightening tool 140 engaged therewith. The fastener tightening tool 140 includes a conventional power tool 142, only the housing of which is shown in the drawing. The conventional power tool 142 has a rotary output driver 144 engageable with a socket member 146. The socket member 146 engages the head 13 of the fastener 10 both electrically and mechanically.

A contact pin 148 is reciprocally mounted to the fastener tightening tool 140 to reciprocate relative to the socket member 146 into engagement with the second electrode 23 interconnected with ultrasonic transducer 19 and the head 13 of the fastener 10. The contact pin 148 is preferably provided with a conductive rubber tip 149 to provide a low acoustic impedance interface while refraining from damaging the ultrasonic transducer 19.

An electronic control device 150, shown only schematically in the drawing, is electrically interconnected with the contact pin 148 and the socket member 146 by electrical lines 152 and 154, respectively, through slip ring wipers 156 and 158—as is well known in the art. Alternatively, the signal may be transferred by a non-contact means, such as by capacitive coupling, and other techniques well-known in the art. The electronic control device 150 supplies and measures electronic differential signals between the first electrode (in this case, head 13) and the second electrode 23 to provide an ultrasonic measurement of the tensile load, stress, or elongation of the fastener 10.

It will be appreciated by those skilled in the art that the fastener tightening tool 140 may be provided with a display device, not shown in the drawing, for displaying ultrasonic measurement of the tensile load, stress, or elongation obtained during the fastener operation. Alternatively, the fastener tightening tool 140 may be adapted to use the information continuously supplied by the electronic control device 150 to determine when a pre-determined amount of tensile load or elongation has occurred and, therefore, when a tightening operation should be stopped.

It will further be appreciated by those skilled in the art that the power tool chosen may, in a manner well-known in the art, monitor other characteristics of the joint being formed, such as the torque and the instantaneous angle of the load indicating fastener. The other information available from the power tool may be combined with the tensile load, stress, or elongation information supplied by the electronic control device 150 to provide a precisely controlled tightening operation in which the various measured parameters are used directly to control the tightening sequence or to monitor the results of the tightening operation. For example, the socket member 146 may be used in conjunction with the power tool using what is known in the art as a "turn of the nut tightening sequence" while the elongation information is used subsequently to determine whether the joint formed by the tightening sequence meets certain specifications.

Although FIG. 10 illustrates a fastener tightening tool 140 incorporating a conventional power tool 142 and electronic control device 150, it will be appreciated by those skilled in the art that a fastener measuring tool may be made incorporating all of the components of the fastener tightening tool except the power tool 142. Such a device may be used to measure the elongation of a fastener independently of the tightening tool.

While the invention has been described with respect to particular embodiments thereof, it is apparent that numerous other forms and modifications of the present invention will be obvious to those skilled in the art. The appended claims and this invention generally should be construed to cover all such obvious forms and modifications which are within the true spirit and scope of the present invention.

I claim:

1. A method of monitoring the load in and imparting torque to a load bearing member comprising the steps of:
   providing a load bearing member subjected to deformation when stressed such that one portion thereof moves relative to another portion thereof, said load bearing member having a first surface functioning as a first electrode and ultrasonic transducer means including an acoustoelectric film grown directly on said first surface adapted to mechanically, electrically and acoustically interconnect said acoustoelectric film to said first surface;
   electrically interconnecting an electronic control to said ultrasonic transducer means for supplying and removing electronic signals to and from said ultrasonic transducer means;
   monitoring said electronic signals received from said ultrasonic transducer means by said electronic control to provide an accurate measurement of said load in said load bearing member; and
   imparting and removing a torque to and from said load bearing member in response to said measurement of said load in said load bearing member.

2. The method of claim 1 wherein said ultrasonic transducer means of said load bearing member provided in said providing step has a second electrode on the exposed surface of said acoustoelectric film adapted to mechanically and electrically interconnect said second electrode to said acoustoelectric film and adapted to electrically isolate said second electrode from said first electrode.

3. The method of claim 2 wherein said load bearing member provided in said providing step has an electrically insulating encapsulating layer extending outward from said second electrode such as to cover exposed surfaces of said acoustoelectric film.

4. The method of claim 1 wherein said acoustoelectric film of said load bearing member provided in said providing step is grown by vapor deposition.

5. The method of claim 1 wherein said acoustoelectric film of said load bearing member provided in said providing step is grown by magnetron sputtering.

6. The method of claim 1 wherein said acoustoelectric film of said load bearing member provided in said providing step is an oriented piezoelectric film chosen from the group consisting of zinc oxide, cadmium sulfide, and aluminum nitride.

7. The method of claim 1 wherein said acoustoelectric film of said load bearing member provided in said providing step is grown with an angle of inclination adapted to allow said ultrasonic transducer means to transmit and receive both longitudinal and transverse ultrasonic waves.

8. The method of claim 2 wherein said second electrode of said ultrasonic transducer means of said load bearing member provided in said providing step is formed by vapor deposition.

9. The method of claim 2 wherein said second electrode of said ultrasonic transducer means of said load bearing member provided in said providing step is chosen from the group consisting of electrically conductive metallic film, paint, and ink.

10. The method of claim 2 wherein said second electrode of said ultrasonic transducer means of said load bearing member provided in said providing step is formed of metallic foil bonded to said acoustoelectric film with an adhesive.

11. The method of claim 1 wherein said acoustoelectric film of said load bearing member provided in said providing step is 1 to 50 microns thick.

12. The method of claim 1 wherein said first surface of said load bearing member provided in said providing step is coated with an electrically conductive film prior to forming said acoustoelectric film on said first surface.

13. The method of claim 1 wherein said load bearing member provided in said providing step has a shank having a longitudinal end with a recess and said first surface is formed in said recess.

14. The method of claim 1 wherein said first surface of said load bearing member provided in said providing step is formed to direct ultrasonic waves from said ultrasonic transducer means grown on said first surface toward an end of said load bearing member remote from said first surface.

15. The method of claim 1 wherein said load bearing member provided in said providing step has a second surface formed at a predetermined distance from said first surface;
   wherein said first surface directs ultrasonic waves from said ultrasonic transducer means, grown on said first surface, toward said second surface; and
   wherein said second surface reflects ultrasonic waves from said ultrasonic transducer means on said first surface back to said ultrasonic transducer means on said first surface.

16. An ultrasonic device for monitoring load, imparting a torque, and removing a torque, said ultrasonic device comprising:
   a load bearing member adapted to deform when stressed and having a first surface functioning as a first electrode and ultrasonic transducer means including an acoustoelectric film grown directly on and conforming to said first surface of said load bearing member so as to mechanically, electrically, and acoustically interconnect said acoustoelectric film to said first surface;
   an electronic control electrically interconnected to said ultrasonic transducer means for supplying and removing electronic signals to and from said ultrasonic transducer means;
   means for monitoring said electronic signals received from said ultrasonic transducer means by said electronic control, said monitoring means providing an accurate measurement of said load in said load bearing member; and
   means for imparting and removing a torque to and from said load bearing member in response to said measurement of said load in said load bearing member.

17. An ultrasonic device as claimed in claim 16 wherein said ultrasonic transducer means further includes a second electrode formed on the exposed surface of said acoustoelectric film in electrical isolation from said first electrode and adapted to mechanically, acoustically, and electrically interconnect with said acoustoelectric film.

18. An ultrasonic device as claimed in claim 17 wherein said second electrode is chosen from the group consisting of electrically conducting metallic film, ink, paint, and foil.

19. An ultrasonic device as claimed in claim 17 further comprising an electrically insulating layer extending over the exposed portions of said first surface, said acoustoelectric film, and said second electrode to exclude contaminants and prevent damage by environmental hazards.

20. An ultrasonic device as claimed in claim 16 wherein said acoustoelectric film is an oriented piezoelectric film chosen from the group consisting of zinc oxide, cadmium sulfide, and aluminum nitride.

21. An ultrasonic device as claimed in claim 16 wherein said acoustoelectric film is 1 to 50 microns thick.

22. An ultrasonic device as claimed in claim 17 wherein said second electrode is 1 to 50 microns thick.

23. An ultrasonic device as claimed in claim 16 further comprising a coating on said first surface between said first surface and said acoustoelectric film.

24. An ultrasonic device as claimed in claim 16 wherein said load bearing member has a recess and said first surface of said load bearing member is located in said recess to protect said ultrasonic transducer means from environmental hazards.

25. An ultrasonic device as claimed in claim 16 wherein said ultrasonic transducer means functions without degradation in performance at the operating temperature of said load bearing member.

26. An ultrasonic device as claimed in claim 16 wherein said ultrasonic transducer means generates high frequency ultrasonic waves between 1 and 500 Mhz, said waves adapted to increase the accuracy and resolution of said device.

27. An ultrasonic device as claimed in claim 16 wherein said acoustoelectric film is an oriented piezoelectric film having an angle of inclination adapted to enable said ultrasonic transducer means to transmit and receive both longitudinal and transverse ultrasonic waves.

28. An ultrasonic device as claimed in claim 16 wherein:
said load bearing member has a second surface which is acoustically reflective;
said first surface of said load bearing member is adapted to direct ultrasonic waves from said ultrasonic transducer means toward said second surface; and
said second surface of said load bearing member is adapted to reflect said waves received from said ultrasonic transducer means back to said ultrasonic transducer means.

29. An ultrasonic device as claimed in claim 16 wherein said load bearing member is a material suitable for transmitting ultrasonic waves.

30. An ultrasonic device for monitoring load, imparting a torque, and removing a torque, said ultrasonic device comprising:
a load bearing member adapted to deform when stressed and having a first surface functioning as a first electrode and ultrasonic transducer means including:
(a) a second electrode, and
(b) an acoustoelectric film grown directly on and conforming to the surface of said second electrode so as to mechanically, electrically, and acoustically interconnect said acoustoelectric film to said second electrode, said acoustoelectric film mechanically, acoustically, and electrically interconnected to said first surface of said load bearing member and adapted to electrically isolate said first electrode from said second electrode;
an electronic control electrically interconnected to said ultrasonic transducer means for supplying and removing electronic signals to and from said ultrasonic transducer means;
means for monitoring said electronic signals received from said ultrasonic transducer means by said electronic control, said monitoring means providing an accurate measurement of said load in said load bearing member; and
means for imparting and removing a torque to and from said load bearing member in response to said measurement of said load in said load bearing member.

31. An ultrasonic device as claimed in claim 30 wherein said second electrode is chosen from the group consisting of electrically conducting metallic film, ink, paint, and foil.

32. An ultrasonic device as claimed in claim 30 further comprising an electrically insulating layer extending over the exposed portions of said first surface, said acoustoelectric film, and said second electrode to exclude contaminants and prevent damage by environmental hazards.

33. An ultrasonic device as claimed in claim 30 wherein said acoustoelectric film is an oriented piezoelectric film chosen from the group consisting of zinc oxide, cadmium sulfide, and aluminum nitride.

34. An ultrasonic device as claimed in claim 30 wherein said acoustoelectric film is 1 to 50 microns thick.

35. An ultrasonic device as claimed in claim 30 wherein said second electrode is 1 to 50 microns thick.

36. An ultrasonic device as claimed in claim 30 further comprising an electrically conductive coating on said surface of said second electrode between said surface and said acoustoelectric film.

37. An ultrasonic device as claimed in claim 30 wherein said load bearing member has a recess and said first surface of said load bearing member is located in said recess to protect said ultrasonic transducer means from environmental hazards.

38. An ultrasonics device as claimed in claim 30 wherein said ultrasonic transducer means functions without degradation in performance at the operating temperature of said load bearing member.

39. An ultrasonic device as claimed in claim 30 wherein said ultrasonic transducer means generates high frequency ultrasonic waves between 1 and 500 MHz, said waves adapted to increase the accuracy and resolution of said device.

40. An ultrasonic device as claimed in claim 30 wherein said acoustoelectric film is an oriented piezoelectric film having an angle of inclination adapted to enable said ultrasonic transducer means to transmit and receive both longitudinal and transverse ultrasonic waves.

41. An ultrasonic device as claimed in claim 30 wherein:

said load bearing member has a second surface which is acoustically reflective;

said first surface of said load bearing member is adapted to direct ultrasonic waves from said ultrasonic transducer means toward said second surface; and said second surface of said load bearing member is adapted to reflect said waves received from said ultrasonic transducer means back to said ultrasonic transducer means.

42. An ultrasonic device as claimed in claim 30 wherein said load bearing member is a material suitable for transmitting ultrasonic waves.

* * * * *